United States Patent [19]

Van Creveld et al.

[11] Patent Number: 5,810,733
[45] Date of Patent: Sep. 22, 1998

[54] ENCAPSULATED ULTRASOUND TRANSDUCER PROBE ASSEMBLY

[75] Inventors: Donald L. Van Creveld, Menlo Park; Richard A. Lyon, Palo Alto; Richard W. Henderson, Fremont, all of Calif.

[73] Assignee: Acuson Corporation, Mountain View, Calif.

[21] Appl. No.: 916,592

[22] Filed: Aug. 22, 1997

Related U.S. Application Data

[63] Continuation of Ser. No. 646,155, May 7, 1996, abandoned.

[51] Int. Cl.$^6$ ...................................................... A61B 8/00
[52] U.S. Cl. ............................................................ 600/459
[58] Field of Search ..................... 600/459, 461, 600/462, 466, 471

[56] References Cited

U.S. PATENT DOCUMENTS

| | | |
|---|---|---|
| 4,951,677 | 8/1990 | Crowley et al. .................. 128/662.06 |
| 5,381,795 | 1/1995 | Nordgren et al. . |
| 5,469,853 | 11/1995 | Law et al. .......................... 128/662.06 |
| 5,476,107 | 12/1995 | Oakley et al. .......................... 128/897 |

*Primary Examiner*—George Manuel
*Attorney, Agent, or Firm*—Ladas & Parry

[57] ABSTRACT

A method of encapsulating an ultrasound transducer assembly probe is disclosed. The encapsulation forms a seamless casing around the entire transducer probe assembly resulting in sealed leak-proof probe conducive to sterilization by immersion in a disinfectant liquid. The encapsulation method of the present invention simplifies the manufacturing process by eliminating several processing steps such as backpotting, welding, backfilling, and strain relief closing of the multiple component prior art construction. The method provides for device that is less expensive to produce, easily repaired and/or upgraded, more reliable, feels more comfortable to the user, and the patient and lends itself readily for mass production.

36 Claims, 4 Drawing Sheets

ENCAPSULATED ULTRASOUND TRANSDUCER PROBE ASSEMBLY

This application is a continuation of U.S. application Ser. No. 08/646,155, filed May 7, 1996, now abandoned.

FIELD OF INVENTION

This present invention relates generally to ultrasound imaging equipment. In particular, it pertains to the manufacture of ultrasound transducers by encapsulation.

BACKGROUND OF THE INVENTION

Ultrasound imaging has become increasingly popular because of its ability to obtain images of internal body organs through non-invasive or minimally invasive techniques. Therefore, it is an ideal choice for many preliminary examinations such as obstetrical or cardiology exams and screenings for certain types of growth irregularities such as tumors without requiring substantial incisions.

Ultrasound imaging systems typically operate by transmitting ultrasound signals through a transducer which contains an array of piezoelectric elements capable of converting an applied voltage into mechanical motion and vice versa. In this way ultrasound acoustic signals can be transmitted into a medium where reflections, caused by impedance mismatches at acoustic interfaces within the medium (e.g. tumors), are received back at the transducer. Received acoustic signals are then converted back to electrical signals which are sent to a signal processor where, among other things, they are amplified and filtered to construct a visual image that can be displayed. The signal processor and display are generally a combined unit whereas the transducer is typically in the form of a hand held probe. The present invention focuses substantially on a method of manufacture of the transducer probe assembly that improves reliability and performance, and reduces cost.

Currently the manufacture of complex devices such as transducer probes typically requires a construction method that involves the integration of multiple components. FIG. 1 shows a perspective view of a typical prior art hand-held transducer probe and generally referred to by reference number 100. Transducer 100 is comprised of multiple machined components including a plastic nosepiece assembly 112 comprised of a plastic nosepiece and acoustic components, an acoustic lens or window 114, a plastic handle portion 116 designed to be grasped by the users hand, a flexible cable 118 for transmitting electrical signals to and from a signal processing unit (not shown), and a strain relief 120 for preventing cable 118 from fraying. Assembly requires that acoustic lens 114 be fitted in nosepiece 112 thereby creating seam 122. Seam 124 is created when nosepiece 112 is fitted to handle portion 116 and seams 126 and 128 are created from the fit between handle portion 116 and strain relief 120 and strain relief 120 and cable 118 respectively. An alternative construction that has been used comprises "clam shell" handle portions creating a seam where the portions meet. The term "seam" used hereinafter will refer to a seam resulting from the joining of separate portions.

Although all components are fitted and adhered with very fine tolerances, a disadvantage with this construction is that seams 122, 124, 126, and 128 do not inherently provide a liquid proof seal thereby discouraging the procedure of immersing the probe in a disinfectant liquid for sterilization. The seams also provide crevices in which bacteria and other contaminants could collect, potentially affecting the sterility of the device. Furthermore, the method of multiple component assembly requires that each of the components be precisely manufactured to fine tolerances which is time consuming and expensive. The requirement of machinability renders it more difficult to shape the device into a more ergonomically form fitting device that fits comfortably in the hand. Further the use of machinable materials often are not optimal in terms of feel and grip. Finally, the adhered components are not easily broken apart without destroying the device. This hampers the effort for repairs and discourages the inclusion of serviceable components within the transducer housing such as semiconductors, switches, indicators etc.

Nordgren et al. in U.S. Pat. No. 5,381,795 disclose a transducer probe design that uses of a rubber-like encapsulated boot around the contact end of the probe to permit immersion in a sterilizing liquid. The Nordgren probe lacks the capacity to be entirely submerged since the handle portion is comprised of two plastic clamshell halves fitted together creating seams that may potentially leak. Further, the electrical connections and terminations between the cable and the flex circuit of the Nordgren probe are not encapsulated thereby potentially limiting immersion of at least this portion. Accordingly, there exists a need for a transducer probe that is inherently sealed from liquid intrusion and therefore permits complete submersion and easy sterilization.

It is a general objective of the present invention to provide a method of manufacture and apparatus that are not subjected to the aforementioned disadvantages and to provide a cost effective procedure suitable for mass production that meets the requirements for immersability.

SUMMARY OF THE INVENTION

To achieve the foregoing and other objectives and in accordance with purpose of the present invention, a method of manufacturing an ultrasound transducer probe assembly is disclosed herein. In accordance with one method of the present invention, the method includes mechanically attaching an acoustic stack array to an internal structure, electrically and mechanically attaching a cable assembly to the stack array thereby forming a sub-assembly, positioning the sub-assembly in a mold, and encapsulating the sub-assembly to form an impermeable rubber-like casing around the entire sub-assembly such that the exterior surface of the casing is seamless and impervious to liquid intrusion.

In an apparatus aspect of the invention, an ultrasound transducer probe includes a contact portion for use in contacting the skin in the target imaging area and a handle portion suitable to be grasped and secured by a hand. The contact and handle portion are integrated into a seamless one-piece unit resulting in a device casing that is completely sealed permitting the probe to be immersed in liquid with no concerns about leaking seams.

Advantages of the present invention include a liquid-proof probe that can be easily sterilized by immersion in a disinfectant. The encapsulation method described further simplifies the manufacturing process by eliminating components in the multiple component assembly construction of the prior art. Several process steps are eliminated from the prior art construction such as welding/sealing, backpotting, backfilling, and strain relief closing. An elastomeric rubber-like casing material, in a preferred embodiment, provides enhanced feel and grip for easier manipulation by the user and improved patient comfort. Repairs can easily be performed by slicing off the casing and re-encapsulating.

Further, the construction method results in a device that is less expensive to produce, more reliable and amenable to mass production. These and other advantages will become apparent upon reading the following detailed descriptions and studying the various figures of the drawings.

BRIEF DESCRIPTION OF THE DRAWINGS

The invention, together with further objects and advantages thereof, may best be understood by reference to the following description taken in conjunction with the accompanying drawings in which.

DETAILED DESCRIPTION OF THE PREFERRED EMBODIMENTS

Figure 1:
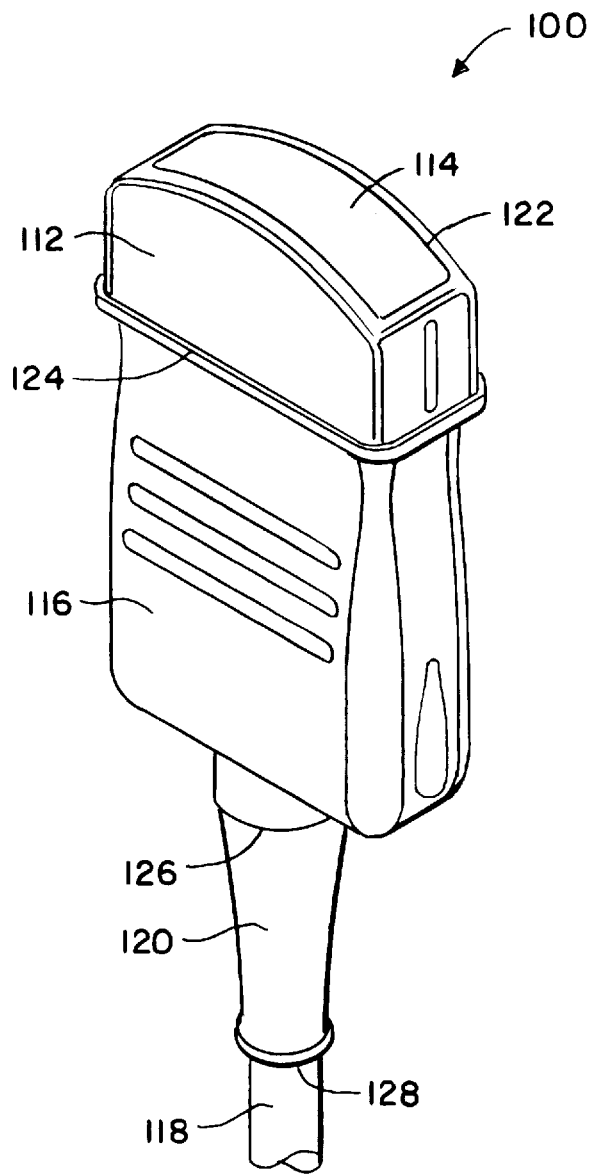
FIG. 1 is a perspective view of a prior art transducer probe assembly.

A discussion of FIG. 1 directed toward a prior art multiple component transducer structure was provided in the preceding sections. In accordance with an embodiment of the present invention, a manufacturing method of encapsulation will described herein. The basic functional components of the transducer described in relation to FIG. 1, comprising an acoustic lens/window 114, a piezoelectric stack array (not shown, located underneath acoustic lens), and cable assembly 118 are also included in the preferred embodiment.

Figure 2:
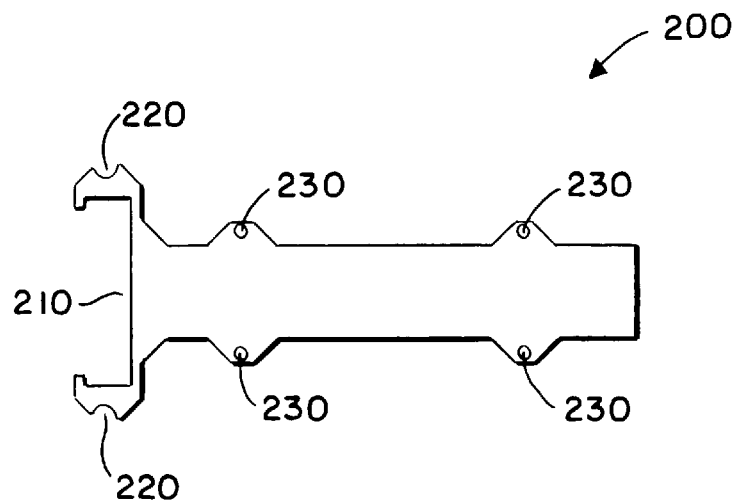
FIG. 2 shows an internal structure in accordance to a preferred embodiment of the present invention.

Referring now to FIG. 2, an internal locating structure 200 is shown that will be used as the foundation for the encapsulation process for a preferred embodiment. Structure 200 provides a rigid member in which to attach the internal components and associated accessories of the transducer. The locating structure also provides an inherently convenient means of positioning acoustic components including the stack array relative to the acoustic lens or window (depicted as element 114 of FIG. 1). The resulting thickness of the acoustic lens or window plays a critical role in ultrasound propagation characteristics such as focal length and transmitted power. For example, a lens that is too thick causes excessive attenuation and reduces the amount of transmitted power. Conversely, a lens that is too thin may cause excessive power to be transmitted through the medium. Since both situations are undesirable, the precise lens thickness is very important. Those skilled in the art are well aware that lens thickness is related to focal length and lenses are manufactured to different thicknesses depending on the depth of focus desired. For example, in a preferred embodiment, the lens thickness approximately in the range of 22 and 80 mils works well for common depths of interest.

Internal structure 200 may be constructed from any rigid material provided that the deformation temperature is above those temperatures of the encapsulation process. By way of example, metals such as aluminum, stainless steel, brass, or even structural plastic may be used. In the preferred embodiment, the internal structure is constructed from an aluminum stamping/punching in a process that is well known in the metal working art. Other forms of construction such as machining, molding, casting etc. may be performed but the relative low cost of stamping makes it the preferred method. Structure 200 includes receptacle 210 provided for receiving an acoustic array. Detents 220 (also referred to as accessory locating features) are provided for locating and supporting accessory devices such as needle guide attachments. Guide holes 230 are provided to permit accurate positioning within the encapsulation mold. All such holes and cavities are easily incorporated in encapsulating process and filled during that time.

Figure 3:
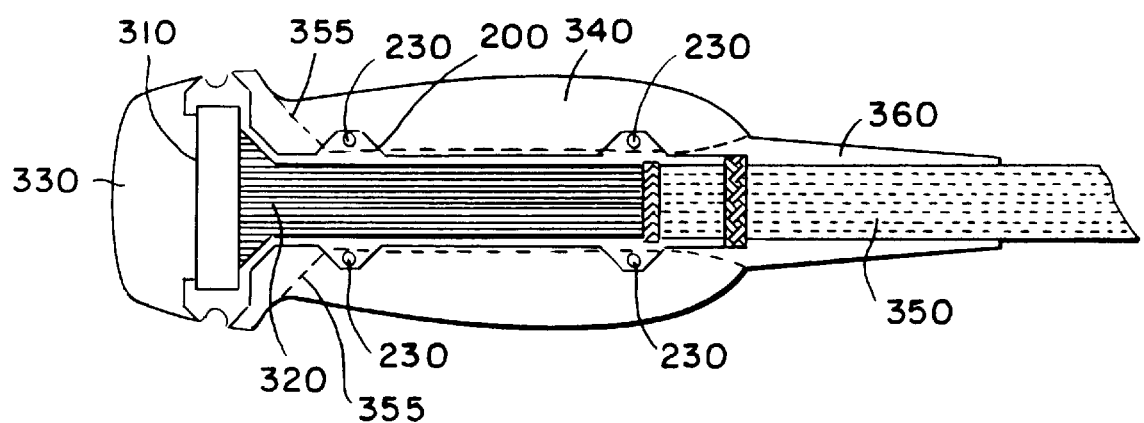
FIG. 3 shows a cross sectional view of the internal structure with attached components after encapsulation in accordance to a preferred embodiment.

Referring now to FIG. 3, a transducer probe formed by encapsulating the structure 200 in accordance with the present invention is shown. The encapsulation process begins by mechanically attaching a shielded transducer stack array 310 to receptacle 210 (FIG. 2) of internal structure 200. A prefabricated cable assembly 320 is then electrically and mechanically attached to stack array 310. The combination of the array 310 and cable 320 attached to structure 200 forms a sub-assembly structure. The sub-assembly along with any thermal devices, mechanical supports, shields, switches indicators or other components are placed into a suitable mold (not shown). Guide holes 230 are aligned with associated guide pins in the mold for precise positioning or locating within the mold to create the acoustically appropriate thickness of lens 330. Other ways of accurately locating the sub-assembly within the mold, such as using computer controlled robot arms, for example, may be used and likewise fall within the scope of the current discussion. The surfaces of the sub-assembly and other items to be encapsulated are prepared by roughing or applying adhesion agents to assure maximum adhesion between the encapsulant and sub-assembly. Typically the encapsulating material, which is sufficiently fluid at room temperature, is injected into the mold. The casting process encapsulates the transducer assembly forming a case material 340 that bonds to cable jacket 350 to provide an environmentally sealed product.

The encapsulating material is typically an acoustically appropriate material for the transducer acoustic lens or window such as Room Temperature Vulcanizing compound (RTV) thus making the casing and lens out of a single cast. By way of example, an RTV part no. Q5-8008 manufactured by Dow-Corning of Midland, Mich. works well in the preferred embodiment. As those skilled in the art will appreciate, RTV has particularly favorable acoustic properties and can be easily cast. In addition, the acoustic impedance of the RTV can be incrementally modified to optimal levels (depending on the specific application) by adding a filler such as silica powder part no. MIN-U-SIL manufactured by US Silica of Berkeley Springs, W. Va. When using a casing material having non-acoustic properties, the lens or window can be formed separately from other suitable acoustic materials such as polyurethanes. For example, polyurethanes such as part no. TDT 178-83 manufactured by Ciba Giegy of East Lansing, Mich. may be used for construction of the lens. Multiple casts or a combination of materials such as rigid castable materials may be used for the case material to provide durability, and possibly may incorporate features to locate and support accessory devices such as needle guides for collecting tissue samples, for example. Rigid castable materials are materials that flow at room temperature but set or harden with time. These are particularly well suited for areas of excessive wear and serve to provide a robust support for accessory devices. An example of a rigid castable that can be used in the present invention is part no. 3101, also known as "Unicast" by Uniroyal Inc. of Middlebury, Conn. Strain relief 360 may be formed integrally with the case housing 340 to reduce the likelihood of cable fraying or degradation. Similarly, any bulges, bumps or indentation patterns may be simultaneously formed in the exterior casing for the purpose of enhancing grip.

A slight variant of the previously described procedure is to perform the encapsulation in multiple steps. Dotted line 355 is shown to illustrate the boundaries between the first and second encapsulation. For example, areas inside line 355 (i.e. all areas excluding handle portion 340), when encapsulated, satisfy the objectives of the present invention in that a sealed sub-assembly unit including acoustic lens 330 is formed. A secondary encapsulation is then performed to form handle portions 340 using guide holes 230 for attachment. The advantage being that various handle materials and shapes can be used and/or replaced on the probe. The multi-encapsulation method allows for easy handle customization to suit various hand sizes. Typical handle sizes are in the range of approximately one to two inches in diameter but may vary significantly depending on the application e.g. obstetrical or cardiology scanning.

Figure 4:
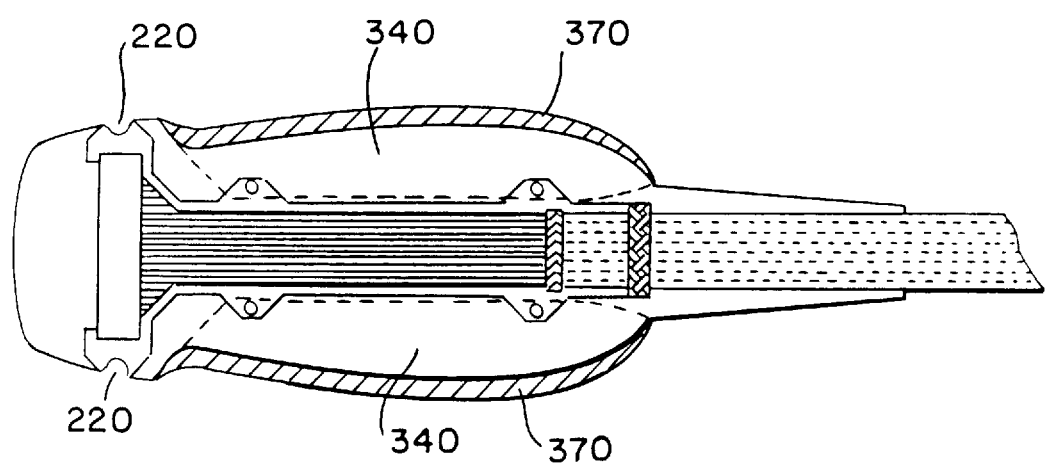
FIG. 4 shows a cross sectional view of the probe of FIG. 3 with attached prefabricated plastic case after encapsulation.

In addition, a prefabricated machined plastic case 370 may be adhered to the encapsulated transducer handle portion 340 as shown in FIG. 4. Enhanced handle properties may also be achieved by applying additional surface treatment steps such as molding, dipping, or coating. Further, surface treatments may be used to form a thin coating around the exterior surface to provide a seamless and inherently sealed device in the case when separate handle portions, prefabricated cases, or separate strain reliefs are used. It should be appreciated by those skilled in the art that a number of manufacturing techniques may be employed to obtain customization for improved handling.

Figure 5:
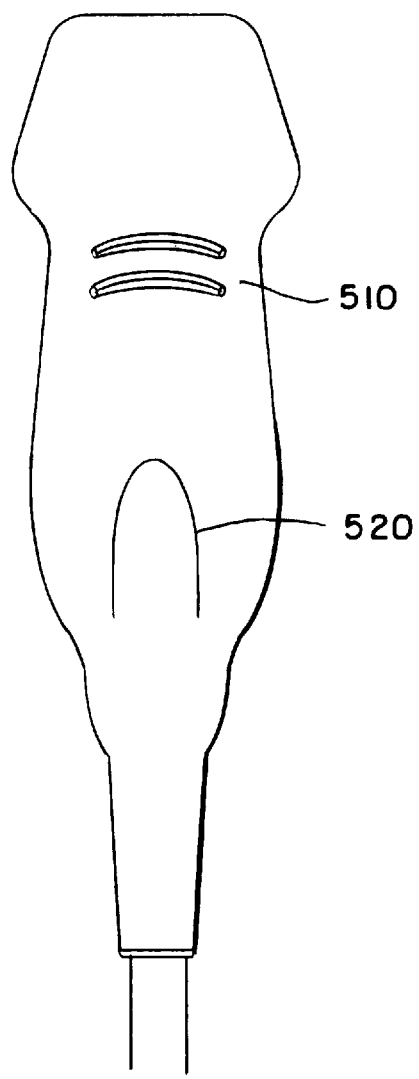
FIG. 5 shows a side view of a preferred embodiment of a seamless encapsulated transducer probe in accordance to the present invention.

FIG. 5 shows the finished product for the transducer assembly made in accordance with a preferred embodiment of the present invention. The encapsulated probe shown, having no attached needle guide option, is inherently sealed from the environment and has no seams. In a probe with an accessory locating feature, such as shown in FIG. 4, detents 220 protrude through the casing material to allow for attachment of a needle guide or other accessories. The device remains sealed since the encapsulant bonds significantly around the detents thereby preserving the liquid-proof seal around the sub-assembly. Grip details 510 and 520 are shown integrated into the case housing for enhanced feel and grip.

In an alternative embodiment, use of internal structure 200 can be omitted. The alternative method includes first forming a mold for a transducer probe by suspending a model of the probe and cable assembly in a container (such as a plastic 1 liter bottle) which is filled with casting material such as RTV compound, rubber, plastic, or even a metal. The container, with the suspended probe, is cured at 50° C. for 12 hours. After curing, the plastic container is cut away and the cable assembly is marked to indicate depth and orientation of the model in the mold. The mold is then cut to remove the model. The cable assembly is electrically and mechanically attached to a transducer stack array.

The array is prepared by sealing any corners with an epoxy such as ITW/Devcon epoxy part no. 1427, Danvers, Mass. The array is then cleaned with isopropyl alcohol and an adhesion promoter is applied such as Dow Corning 1200 Prime Coat, Midland, Mich., to ensure bonding to the lens material. The inside of the mold is coated with a mold release material to prevent adhesion of the encapsulation material to the mold during curing. The array and attached cable assembly are then suspended in the mold cavity using the markings on the cable to identify orientation and depth. RTV material is dispensed at room temperature into the mold using a caulking gun-like pneumatic tool to encapsulate the components. The mold is left to set at room temperature for 1 hour and then placed into an oven at 50° C. for at least 12 hours until fully cured. The fabricated probe is finally removed from the mold and is ready for use.

Advantages of the present invention are that the probe provides liquid submersibility for easy sterilization, permitting use in surgical applications or in any procedure in which cleaning and disinfecting after exposure to body fluids is required. Another advantage is that some process steps required in the prior art construction such as backpotting, welding, backfilling, and strain relief closing are correspondingly eliminated. Further, cumbersome components such as the nosepiece, rear case housing, weld ring and backpotting material are eliminated. In addition, probe casings that are cast eliminate the need for machined casings designed specifically to incorporate the cable assembly termination block thereby reducing costs and simplifying production.

The ergonomic quality of the device is improved through the use of rubber-like encapsulants that provide the user and patient with a high level of comfort during clinical use. Further, complex surface forms that improve comfort can be more easily cast than machined. The device of the present invention is inherently more reliable than prior art devices since contaminants will not easily leak into the transducer and damage internal components. Repairs and/or upgrading functionality can be readily performed by slicing off the casing, performing repairs and/or upgrade and then re-encapsulating. The manufacturing method described herein circumvents many of the shortcomings of prior designs and lowers the cost of each transducer assembly through eliminated components and reduced finishing time.

Although only two embodiments of the present invention have been described in detail, it should be understood that the present invention may be constructed with process steps performed in other sequences with optional steps added or eliminated without departing from the spirit or scope of the invention. In particular, other methods may be used such as molding, dipping, and coating. Therefore the present examples are to be considered as illustrative and not restrictive, and the invention is not to be limited to the details given herein, but may be modified within the scope of the appended claims.

What is claimed is:

1. A method of manufacturing an ultrasound transducer probe having an internal structure; and a continuous liquid-impermeable solid casing permanently surrounding the structure and defining a contact portion and a handle portion, the handle portion being integrally formed with the contact portion and being shaped to be grasped by the hand of a user to control the placement and movement of the contact portion for use in contacting skin at a target area, wherein immersion of the casing in liquid for cleaning leaves the structure unexposed to the liquid, the method comprising the steps of:

attaching a transducer stack array to an internal locating structure to form the internal structure;

attaching a cable assembly to the stack array such that a suitable electrical connection is formed, wherein the combined cable assembly and internal structure forms a sub-assembly;

positioning the sub-assembly within a mold; and encapsulating the sub-assembly to form the solid casing around the sub-assembly such that the exterior surface of the casing is substantially continuous and impervious to liquid intrusion.

2. The method of manufacturing as recited in claim 1 wherein positioning of the subassembly includes fitting associated guide pins in the mold to guide holes in the internal structure.

3. The method of manufacturing as recited in claim 1 wherein the encapsulation is formed by casting.

4. The method of manufacturing as recited in claim 1 wherein a second encapsulation is performed around the sub-assembly for forming a customized handle which becomes the handle portion.

5. The method of manufacturing as recited in claim 4 wherein a prefabricated case is further adhered to the handle portion.

6. The method of manufacturing as recited in claim 1 wherein the method includes the step of dipping.

7. The method of manufacturing as recited in claim 1 wherein the method includes the step of coating.

8. The method of manufacturing as recited in claim 1 wherein positioning of the sub-assembly includes fitting associated guide pins in the mold to guide holes of the internal structure.

9. The method of manufacturing as recited in claim 1 wherein positioning of the subassembly into the mold is performed by a computer automated procedure.

10. An ultrasound transducer probe having interior transducer probe components, the probe comprising:
    a substantially continuous one-piece casing for permanently encapsulating the interior transducer probe components, the casing having:
        a contact portion for use in contacting skin at a target area, the contact portion having a lens; and
        a handle portion extending from the contact portion, the handle portion being shaped for grasping by the hand of the user; the probe further having
    a power connection sealed to or integrated with the casing, wherein the contact portion and the handle portion are integrated into the substantially continuous one-piece casing resulting in the casing being sealed and associated with the power connection so as to permit liquid immersion of the casing and the power connection.

11. The ultrasound transducer probe as recited in claim 10 wherein the casing is RTV polymer.

12. The ultrasound transducer probe according to claim 11 wherein the RTV polymer compound employs a filler for modifying acoustic impedance of the RTV polymer compound.

13. The ultrasound transducer probe according to claim 12 wherein the filler is silica powder.

14. The ultrasound transducer probe as recited in claim 10 wherein the casing is a polyurethane.

15. The ultrasound transducer probe as recited in claim 10 wherein the contact portion comprises as the lens a surface of an acoustic lens from a polyurethane.

16. The ultrasound transducer probe as recited in claim 10 wherein needle guide locating features protrude through the casing for external attachment of a needle guide.

17. The ultrasound transducer probe as recited in claim 10 wherein a needle guide is incorporated in the device casing.

18. The ultrasound transducer probe as recited in claim 10 wherein the handle portion is ergonomically shaped to reduce fatigue for extensive continuous use.

19. The ultrasound transducer probe as recited in claim 10 wherein the handle portion includes grip enhancing protrusion and indentation patterns.

20. An ultrasound transducer probe as recited in claim 10 wherein the power connection includes a cable, the handle portion having a bottom, a strain relief being integrated into the bottom and cooperating with the cable for preventing cable degradation.

21. A method of manufacturing the probe of claim 10 wherein the components include a transducer stack array and the power connections includes a cable assembly, the method comprising attaching the transducer stack array to the cable assembly such that a suitable electrical and mechanical connection is formed, positioning the stack array and attached cable assembly to form the casing therearound, wherein the exterior surface of the casing is impervious to liquid intrusion.

22. The method of manufacturing as recited in claim 21 wherein the mold is formed by casting a model of a transducer probe.

23. The method of manufacturing as recited in claim 22 wherein the cast material is one of RTV compound, rubber, plastic, metal.

24. The method of manufacturing as recited in claim 23 wherein the mold is cured in an oven at about 50 degrees C for approximately 12 hours.

25. The method of manufacturing as recited in claim 21 wherein the cable assembly is marked for orientation within the mold.

26. The method of manufacturing as recited in claim 25 wherein the orientation markings are used for positioning in the mold.

27. The method of manufacturing as recited in claim 26 wherein the mold is cured in an oven at about 50 degrees C for approximately 12 hours thereby forming a usable device.

28. The method of manufacturing as recited in claim 21 wherein the stack array is prepared by sealing the corners with an epoxy with an adhesion promoter to ensure bonding to the lens material.

29. An encapsulated ultrasound transducer probe comprising a contact portion, a handle portion, and accessory locating features wherein the encapsulation forms a liquid-proof casing around the probe, and further wherein said locating feature protrude through the casing for attachment of an accessory device.

30. The encapsulated ultrasound transducer probe as recited in claim 29 wherein the attached accessory device is a needle guide.

31. The encapsulated ultrasound transducer probe as recited in claim 29 wherein the probe further includes a plastic casing adhered to the handle portion.

32. The encapsulated ultrasound transducer probe as recited in claim 29 wherein the encapsulation is RTV.

33. The encapsulated ultrasound transducer probe as recited in claim 29 wherein the encapsulation is a polyurethane.

34. A probe having interior components electrically connected to a cable, the probe comprising:
    a substantially continuous liquid-impermeable encapsulate comprised of a solid piece of material permanently and sealingly surrounding the components such that upon immersion of the encapsulate in liquid the components remain dry, the encapsulate defining a first end; a second end opposite the first end; and a handle portion extending between the first end and the second end, the first end, second end and handle portion being integrally formed, the first end being a lens carrying end and having a width and a length, the width varying along the length such that the width of the first end increases toward the handle portion; the handle portion being elongate and shaped for gripping by the human hand, the handle portion having a handle width near the first end and a handle width near the second end, the handle width near the first end being less than the handle width near the second end and less than the width of the first end near the handle portion; the second end surrounding and being permanently bonded in a liquid tight fashion to the cable; the second end having a length and a width, the width varying along the length of the second end, the width of the second end being greatest near the handle portion, the probe being an ultrasound transducer probe for direct gripping and control by the hand of the user on the skin, the shape of the handle portion being ergonomically fashioned to reduce fatigue by the user, the probe being immersible in liquid for the cleansing of the encapsulant.

35. An ultrasound assembly comprising:

a liquid-impermeable, substantially continous outer casing, the casing being permanently connected around and housing in a liquid impermeable fashion interior components, the casing defining:
  a contact portion; and
  a handle portion extending from the contact portion and integrally connected thereto, the handle portion being shaped to be grasped by the hand of the user for movement and placement of the contact portion for contacting skin at a target area, wherein the casing with the components held therein is immersible in liquid without the liquid contacting the components.

36. An ultrasound transducer probe having interior components comprising:

a rubber-like, liquid impermeable casing permanently and sealingly surrounding the interior components of the ultrasound transducer probe to act as a bar between the components and liquids, the casing being comprised of:
  a contact portion for use in contacting the skin at a target area, the contact portion having a lens therein with a thickness of between about 22 and about 80 mils;
  a handle portion for grasping by the hand of the user, the handle portion having a diameter of between about one to about two inches and being shaped to ergonomically reduce fatigue by the user during use of the probe; and
  a cable extending from the handle portion, wherein the contact portion and the handle portion are integrated into a substantially continuous one-piece unit resulting in the casing encapsulating the interior components and being sealed to or integrated with the cable to permit liquid immersion of the contact and handle portion and the cable without damage thereto by the liquid.

* * * * *